United States Patent [19]

Yamazaki et al.

[11] Patent Number: 5,980,924
[45] Date of Patent: Nov. 9, 1999

[54] SKIN CLEANSING SHEET

[75] Inventors: Ritsuko Yamazaki; Reiko Fukuda; Isao Umemoto, all of Tokyo; Manabu Kaneda; Yasuhiro Komori, both of Ichikai-machi, all of Japan

[73] Assignee: Kao Corporation, Tokyo, Japan

[21] Appl. No.: 09/044,023

[22] Filed: Mar. 19, 1998

[30] Foreign Application Priority Data

| Apr. 9, 1997 | [JP] | Japan | 9-090689 |
| May 8, 1997 | [JP] | Japan | 9-117923 |
| Jun. 4, 1997 | [JP] | Japan | 9-146271 |

[51] Int. Cl.$^6$ .................................................. A01N 25/34
[52] U.S. Cl. ........................................... 424/402; 424/401
[58] Field of Search .................................... 510/136, 137, 510/138, 159, 403; 424/401, 402

[56] References Cited

U.S. PATENT DOCUMENTS

| 4,514,385 | 4/1985 | Damani et al. | 424/81 |
| 4,891,228 | 1/1990 | Thaman et al. | 424/443 |
| 5,756,437 | 5/1998 | Yamazaki et al. | 510/136 |

FOREIGN PATENT DOCUMENTS

327326 A1  8/1989  European Pat. Off. .

*Primary Examiner*—Shelley A. Dodson
*Assistant Examiner*—Kathryne E. Shelborne
*Attorney, Agent, or Firm*—Oblon, Spivak, McClelland, Maier & Neustadt, P.C.

[57] ABSTRACT

The invention relates to a skin cleansing sheet obtained by impregnating (c) a sheet with an aqueous composition containing (a) 1–50 wt. % of a nonionic surfactant having an HLB of 10–16 and (b) 1–30 wt. % of a polyhydric alcohol or glycol ether. The cleansing sheet has high detergency and detergent speed to smears of makeup and sebum, and low irritativeness to the skin, gives users a pleasant feeling upon use, and moreover has good handling property and stability.

10 Claims, 1 Drawing Sheet

SKIN CLEANSING SHEET

BACKGROUND OF THE INVENTION

1. Field of the Invention

The present invention relates to a skin cleansing sheet which has high detergency to smears of makeup and sebum, low irritativeness to the skin, excellent handling property and good stability.

2. Description of the Background Art

Since makeup cosmetics such as lipsticks, foundations, eye shadows and mascaras contain a great amount of oil and fat, they cannot be sufficiently solubilized or emulsified with a solid or pasty facial soap comprising ordinary soap as a main component. It is therefore difficult to remove a smear of makeup with such a facial soap. In order to remove such a smear of makeup, gelled detergent compositions, cleansing creams, cleansing oils and the like, which are composed mainly of an oily base, have heretofore been used.

However, these cleansing compositions composed mainly of the oily base cannot sufficiently cleanse smears of sebum including a solid smear filled in pores of the skin and also give a feeling of oil. Therefore, it has been necessary to wash the face again with a pasty facial soap or the like after cleansing with the cleansing composition. The cleansing compositions composed mainly of the oily base involve a problem that when they are used at a place of high temperature and humidity, they absorb moisture to deteriorate their stability, and so separation and reduction in detergency are caused.

Detergent compositions for removing oily smears such as smears of makeup and sebum are also required to have low irritativeness to the skin. However, ordinary fatty acid soap and detergent compositions comprising an anionic surfactant as a base generally have high irritativeness to the skin. Even when a nonionic surfactant, which has low irritativeness and good detergency, is used as a base, there have been problems that when a thickening agent is added like detergent compositions on the market at present, the detergent speed of the surfactant is markedly lowered, and the resultant detergent composition has a slimy feel upon use. If the thickening agent is not used for the purpose of avoiding such demerits resulted from the thickening agent, the viscosity of the system becomes low, and so the handling property of the resulting detergent composition is impaired, resulting in its flowing out of a face upon washing the face to stain clothes and/or the like.

SUMMARY OF THE INVENTION

Accordingly, it is an object of the present invention to provide a skin cleansing sheet which has high detergency and detergent speed to smears of makeup and sebum and low irritativeness to the skin, gives users a pleasant feeling upon use, and moreover has good handling property and stability.

In view of the foregoing circumstances, the present inventors have carried out an extensive investigation. As a result, it has been found that a skin cleansing sheet obtained by impregnating a sheet with an aqueous composition containing a specific nonionic surfactant and a polyhydric alcohol or glycol ether has high detergency and detergent speed to oily smears such as smears of makeup and sebum and low irritativeness to the skin, gives users a pleasant feeling upon use, and moreover has good handling property and stability. It has also been found that when a certain amount of a salt is added to the aqueous composition, not only the detergency and detergent speed are more enhanced, but its stability is also improved, and that this salt-containing aqueous composition is excellent for a skin detergent composition even when it is used by an ordinary washing method, to say nothing of the case where it is impregnated into a sheet for use, thus leading to completion of the present invention.

According to the present invention, there is thus provided a skin cleansing sheet obtained by impregnating (c) a sheet with an aqueous composition containing (a) 1–50 wt. % of a nonionic surfactant having an HLB of 10–16 and (b) 1–30 wt. % of a polyhydric alcohol or glycol ether.

According to the present invention, there is also provided an aqueous skin detergent composition comprising the following components (a), (b) and (d):

(a) 1–50 of a nonionic surfactant having an HLB of 10–16;

(b) 1–30 wt. % of a polyhydric alcohol or glycol ether; and (d) 0.1–10 wt. % of a salt.

The skin cleansing sheet according to the present invention has high detergency and detergent speed to oily smears such as smears of makeup and sebum in spite of its low irritativeness to the skin, gives users a pleasant feeling upon use because it neither gives a feeling of remaining after use nor has a slimy feel, and moreover has good handling property and stability.

The above and other objects, features and advantages of the present invention will be readily appreciated as the same becomes better understood from the preferred embodiments of the present invention, which will be described subsequently in detail, and from the appended claims.

DETAILED DESCRIPTION OF THE PREFERRED EMBODIMENTS

Figure 1:
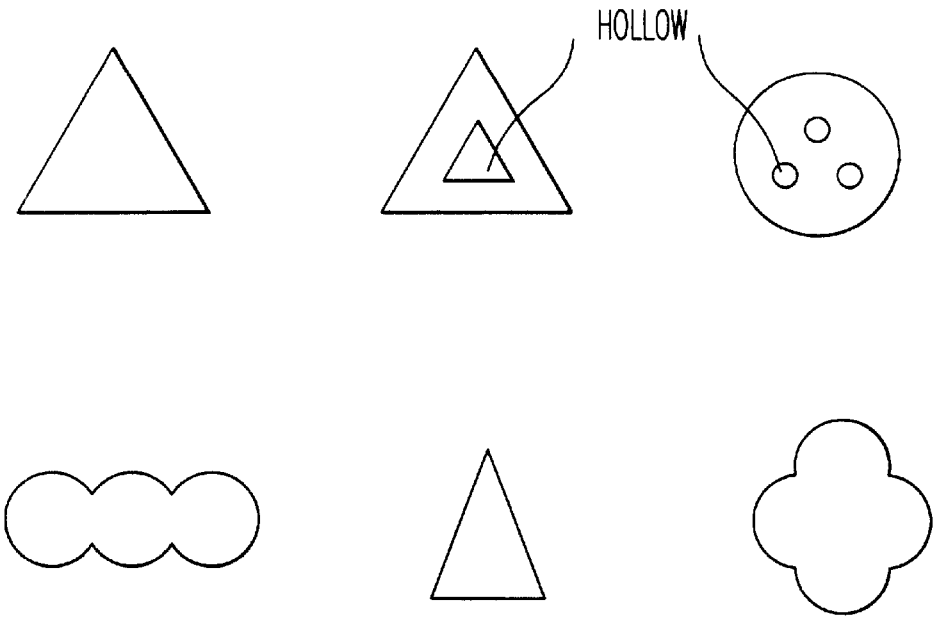
FIG. 1 illustrates cross-sections of fibers used for sheets.

The nonionic surfactant of the component (a) useful in the practice of the present invention has an HLB of 10–16, preferably 12–14. Any nonionic surfactant having an HLB lower than 10 is difficult to use in an aqueous system. On the other hand, any nonionic surfactant having an HLB exceeding 16 cannot bring about sufficient detergency.

Incidentally, HLB is an index to hydrophile-lipophile balance. In the present invention, a value calculated out in accordance with the following equation by Oda and Teramura is used.

$$HLB = \frac{\sum \text{Organicity value}}{\sum \text{Inorganicity value}}$$

No particular limitation is imposed on the nonionic surfactant of the component (a) so far as it is that used in the classical detergent compositions. However, polyethylene glycol higher fatty acid esters represented by the following general formula (1) are particularly preferred because of its lower irritativeness to the skin.

$$RCOO-(CH_2CH_2O)_n-H \quad (1)$$

wherein RCO is a saturated or unsaturated acyl group having 4–30 carbon atoms, and n is a number of 1–50 on the weight average.

In the formula, RCO is a saturated or unsaturated acyl group having 4–30 carbon atoms. In particular, a group having 10–20 carbon atoms, for example, a caprinoyl, lauroyl, myristoyl, palmitoyl or stearoyl group, is preferred. Further, n is a number of 1–50 on the weight average. In particular, a number of 10–30 is preferred because a cleansing sheet or aqueous detergent composition more enhanced in detergency can be provided.

The nonionic surfactants of the component (a) may be used either singly or in any combination thereof and are incorporated in a proportion of 1–50 wt. %, preferably 3–20 wt. %, particularly preferably 5–15 wt. % in the aqueous composition. If the proportion of the component (a) is lower than 1 wt. %, sufficient detergency cannot be achieved. On the other hand, any proportion higher than 50 wt. % results in a skin cleansing sheet or aqueous detergent composition which has a sticky or slimy feel and hence gives users an extremely unpleasant feeling upon use.

The component (b) used in the present invention is a polyhydric alcohol or glycol ether. Examples of the polyhydric alcohol include ethylene glycol, propylene glycol, isoprene glycol, dipropylene glycol, 1,3-butylene glycol, diethylene glycol, glycerol, pentaerythritol and sorbitol. Examples of the glycol ether include ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, diethylene glycol monopropyl ether, diethylene glycol monobutyl ether, propylene glycol monomethyl ether, propylene glycol monoethyl ether and ethylene glycol monophenyl ether.

Of these, ethylene glycol, propylene glycol, isoprene glycol, dipropylene glycol, glycerol, 1,3-butylene glycol, sorbitol and diethylene glycol monoethyl ether are particularly preferred from the viewpoint of a feeling upon use. Further, glycerol and sorbitol are preferred from the viewpoints of detergency and low irritativeness.

As the component (b), may be used one selected from among these polyhydric alcohols and glycol ethers or a combination thereof. The component (b) is incorporated in a proportion of 1–30 wt. %, preferably 2–20 wt. %, particularly preferably 5–15 wt. % in the aqueous composition. If the proportion of the component (b) is lower than 1 wt. %, sufficient detergency cannot be achieved. On the other hand, any proportion higher than 30 wt. % results in a skin cleansing sheet or aqueous detergent composition which gives users a heavy feeling upon use.

It is preferable that (d) a salt be further added in a proportion of 0.1–10 wt. % to the aqueous composition, because the detergency, detergent speed, feeling upon use and stability under high temperature and humidity conditions of the resulting skin cleansing sheet or aqueous detergent composition can be enhanced.

No particular limitation is imposed on the salt of the component (d) used in the present invention so far as it is soluble in water. Any of organic salts and inorganic salts may be used. Specific examples thereof include:

the sulfates of metals selected from among Groups 1A, 2A, 2B and 3B of the periodic table, the sulfates of non-metallic ions and alkali metal carbonates;

the sulfates of metals selected from Group 1B of the periodic table, alum, alkali metal hydrogencarbonates, alkali metal tripolyphosphates and pyrophosphates, sodium chloride, potassium chloride, ammonium chloride, and alkali metal silicates; and the citrates, tartrates, succinates and carboxymethyloxy succinates of metals selected from among Groups 1A, 2A, 2B and 3B of the periodic table as well as the citrate, tartrate, succinate and carboxymethyloxy succinates of an ammonium ion.

Of these, the sulfates and chlorides of metals selected from among Groups 1A (preferably, sodium and potassium), 2A (preferably, magnesium and calcium), 2B (preferably, zinc) and 3B (preferably, boron and aluminum) of the periodic table are preferred, with sodium chloride, potassium chloride and sodium sulfate being particularly preferred because they have high solubility in water, and the detergency of the resulting skin cleansing sheet or aqueous detergent composition can be more enhanced.

The salts of the component (d) may be used either singly or in any combination thereof and are incorporated in a proportion of 0.1–10 wt. %, preferably 0.5–5 wt. %, particularly preferably 1–3 wt. % in the aqueous composition. If the proportion of the component (d) is lower than 0.1 wt. %, sufficient detergency cannot be achieved. If the proportion exceeds 10 wt. % on the other hand, the system becomes markedly unstable, and so separation in the system easily occurs even at room temperature.

In the aqueous compositions used in the present Invention, ingredients commonly used in the classical detergent compositions, for example, moisturizers, germicides, antiseptics, chelating agents, electrolytes, medicinally-effective agents, coloring matter, perfume bases, antioxidants and pH adjustors, may be suitably incorporated in addition to the above-described essential components so far as no detrimental influence Is thereby imposed on the effects of the present invention.

The aqueous compositions used in the present invention are prepared by mixing the individual components with water in accordance with a method known per se in the art.

In the present invention, the aqueous composition obtained in the above-described manner is impregnated into (c) a sheet, whereby the stability of the composition can be more enhanced than it is stored in the form of liquid.

No particular limitation is imposed on the sheet (c) used herein. For example, either woven fabric or nonwoven fabric of natural fibers or synthetic fibers may be used. Specific examples thereof include woven fabrics and nonwoven fabrics of rayon, acetate, acrylic, polyester, polyethylene, polypropylene, polyurethane, polyamide, cotton and the like, and tissue paper (made of natural pulp).

Of these, nonwoven fabrics (made of natural or synthetic fibers) of hydrophilic fibers, for example, cotton or rayon, are preferred in that their production and touch are easy to control. Nonwoven fabrics made of natural fibers are more preferred in that they are good to the touch.

The average basis weight of the sheet (c) is preferably within a range of 20–120 g/m$^2$, more preferably 30–100 g/m$^2$, most preferably 40–80 g/m$^2$ in that a skin cleansing sheet having a better feel upon use and undergoing no strike through of smears wiped off can be obtained.

When a nonwoven fabric, wherein (1) the content of cellulose is at least 50 wt. %;

(2) the average basis weight is 20–120 g/m$^2$;

(3) the average fineness of constituent fibers is at most 3 d (deniers);

(4) it is a nonwoven fabric fabricated by water-jet inter-minglement; and (5) the reflectance is at least 45% when measured in a dry state, is used as the sheet (c), a skin cleansing sheet, which has excellent retention of the aqueous detergent composition therein and high detergency to oily smears such as smears of makeup and sebum, scarcely strike through smears and gives users a pleasant feeling upon use, can be obtained. It is hence preferable to use such a nonwoven fabric.

The content of cellulose in the nonwoven fabric used as the sheet (c) is preferably at least 50 wt. %, particularly at least 70 wt. % in that the aqueous detergent composition can be retained well.

In the nonwoven fabric, fiber components other than cellulose include various kinds of synthetic fibers, for example, fibers made of polyolefin resins such as polypropylene and polyethylene, fibers made of polyester resins, polyacrylic resins and polyamide resins such as nylon, fibers made of copolymers and modified products of these resins, and synthetic fibers containing titanium oxide in a proportion of at least 0.5 wt. %, preferably 0.5–5 wt. %, more preferably 1–5 wt. %. Any combination of these fibers may be used.

Figure 2:
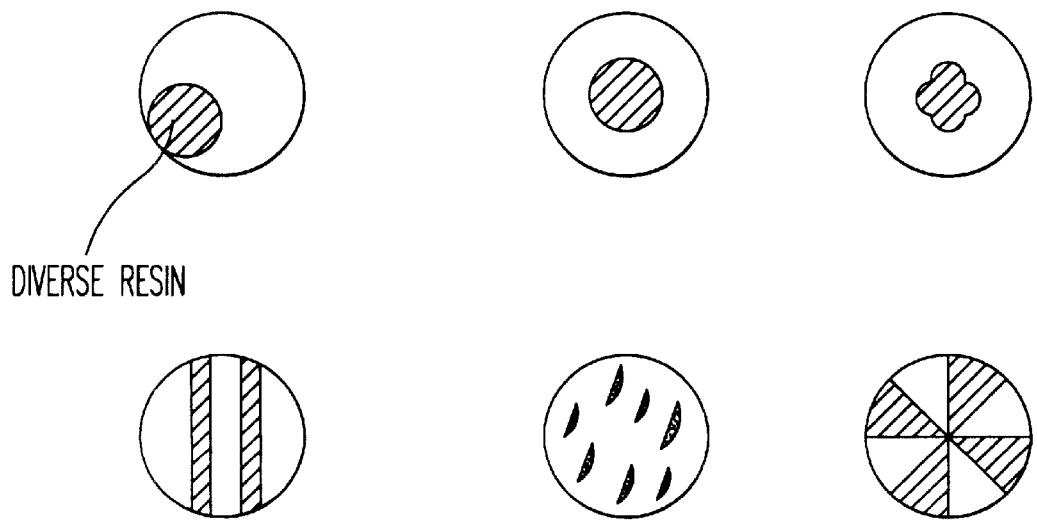
FIG. 2 illustrates cross-sections of conjugated fibers used for sheets.

The fibers making up the nonwoven fabric may be either in the form of a uniform circle in section or in the form of a triangle, star, quatrefoil or cloud in section, or may have a hollow modified cross-section or a cross-section of conjugated fiber composed of a combination of cellulose and a synthetic fiber (see FIGS. 1 and 2). Even when the fibers having the cross-section of conjugated fiber are used, it is only necessary for the fibers to contain cellulose in a proportion of at least 50 wt. %.

The average basis weight of the nonwoven fabric is preferably within a range of 20–120 g/m$^2$, more preferably 30–100 g/m$^2$, most preferably 40–80 g/m$^2$ in that a skin cleansing sheet having a better feel upon use and undergoing no strike through of smears wiped off can be obtained. The average basis weight can be determined by measuring the weight of the fabric per unit area (1 m$^2$) in accordance with a method known per se in the art.

The average fineness of constituent fibers of the nonwoven fabric is preferably at most 3 d (deniers), more preferably at most 2 d, most preferably at most 1.5 d in that a cleansing sheet having the good ability to wipe off smears and high detergency can be provided. The average fineness is determined by measuring the thickness of fibers through a microscope and averaging the measured values.

When fibers having an average fineness of about 1.5–3 d are used, it is preferable to use extra fine fibers having an average fineness of at most 1.0 d in combination from the viewpoint of the ability to wipe off smears.

The nonwoven fabric is fabricated by water-jet interminglement. This production method is preferable in that a nonwoven fabric good to the touch is obtained.

The reflectance of the nonwoven fabric is preferably at least 45%, more preferably at least 50%, most preferably at least 60% when measured in a dry state in that smears are scarcely struck through, and so a virgin surface of the cleansing sheet is hard to smear. The reflectance is determined in the following manner. Namely, the measurement is conducted 5–10 times at a wavelength of 500 nm by means of an SZ-Σ80 color-difference meter manufactured by Nippon Denshoku Kogyo K.K. selecting the following measuring conditions: a lens 30 mm in diameter, sample stand, light source C/2 and a spectral curve-reflectance mode, and the measured values are averaged.

The distribution of the constituent fibers of this nonwoven fabric may be such that homogeneous fibers are dispersed or that fibers different from each other in thickness, kind, nature and the like are mixed at random. However, it is preferable that the fibers different from each other in thickness, kind, nature and the like be distributed laminarly in the direction of thickness from the viewpoints of the ability to wipe off smears and anti-striking through. For example, (1) a two-layer fabric composed of a wiping layer formed mainly of rayon having a fineness of 0.8–1.5 d and a shielding layer (high opacifying layer) composed of one of a synthetic fiber containing 1–5 wt. % of $TiO_2$, an extra fine fiber by a melt blown method and a divided fiber, or a combination of two or more of them; (2) a three-layer fabric of sandwich structure that an additional wiping layer is applied to the fabric of the construction (1); and (3) a multi-layer fabric of 4 or more layers may preferably be used.

No particular limitation is imposed on a method for impregnating the sheet (c) with the aqueous composition. It is however preferable to impregnate the sheet (c) with the aqueous composition to a pickup of 1–10 g/g, particularly 2–5 g/g by, for example, spraying, because a skin cleansing sheet having good detergency and feel upon use can be obtained.

The aqueous composition containing the components (a), (b) and (d) may be directly used as a skin detergent composition without being impregnated into the sheet. For example, it may be used for a facial or cleansing soap. In particular, it is suitable for use as a detergent composition for removing makeup cosmetics.

The present invention will hereinafter be described in more detail by the following Examples. However, the present invention is not limited to these examples only.

EXAMPLE 1

Aqueous compositions having their corresponding formulations shown in Tables 1 to 3 were prepared in accordance with a method known per se in the art. These compositions were impregnated into their corresponding sheets shown in Tables 1 to 3 to obtain skin cleansing sheets. The skin cleansing sheets thus obtained were evaluated as to detergency, detergent speed, handling property, feeling upon use, irritativeness to the skin and stability. The results are shown in Tables 1 to 3.

Evaluation Methods (1) Detergency:

A certain amount of a lipstick was applied to the inner side of a human lower arm, and the lipstick was wiped off predetermined times with each of the cleansing sheets under a fixed pressure. In the case of liquid detergent compositions, the lipstick was removed by massaging the smeared site the predetermined times with each of the detergent compositions under the fixed pressure and then rinsing out the detergent composition. A color difference between before and after the removal of the lipstick was measured to determine the detergency in terms of percentage of color difference. The detergency was ranked in accordance with the following standard:

◯: Not lower than 70%;

Δ: Not lower than 50%, but lower than 70%;

X: Lower than 50%.

(2) Detergent speed:

The number of times of wiping or massage required to exhibit the detergency of 70% as calculated out by the above measuring method (1) when a certain amount of a lipstick was applied to the inner side of a human lower arm, and the lipstick was wiped off with each of the cleansing sheets under a fixed pressure, or the lipstick was removed by massaging the smeared site with each of the liquid detergent compositions under the fixed pressure was determined, and the detergent speed was ranked in accordance with the following standard:

○: Less than 5 times;
Δ: 5 to 9 times;
X: Not less than 10 times.

(3) Handling property:

Expert panelists evaluated the cleansing sheets and liquid detergent compositions as to easiness of handling when each of the samples was applied to the faces of the panelists. The handling property was ranked in accordance with the following standard:

○: Easy to use without the liquid detergent flowing out of the face;
X: Hard to use with the liquid detergent flowing out of the face.

(4) Feeling upon use:

Expert panelist organoleptically evaluated the cleansing sheets and liquid detergent compositions as to feeling upon use such as a feeling of remaining after wiping with each of the cleansing sheets or washing with each of the liquid detergent compositions, slimy feel and refreshed feeling. The feeling upon use was ranked in accordance with the following standard:

◎ : Very good;
○: Good (preferable);
Δ: Fair;
X: Poor (unpreferable).

(5) Irritativeness to the skin:

Cultured cells derived from a rabbit cornea were used to determine a concentration ($IC_{50}$) of each sample required to inhibit growth of the cells by 50%, and the irritativeness to the skin was ranked in accordance with the following standard:

Weak irritation: $IC_{50}$ was not lower than 500 ppm;
Medium irritation: $IC_{50}$ was not lower than 200 ppm, but lower than 500 ppm;
Strong irritation: $IC_{50}$ was lower than 200 ppm.

(6) Stability:

Each of the cleansing sheets and liquid detergent compositions was stored in a thermostatic chamber controlled at a varied temperature between 50° C. and −5° C. to observe their appearances after 1 month. The stability was ranked in accordance with the following standard:

○: Good at the overall temperature;
Δ: Underwent a change in appearance according to the temperature;
X: Separation occurred.

TABLE 1

| Component (wt. %) | Invention product | | | | | | |
|---|---|---|---|---|---|---|---|
| | 1 | 2 | 3 | 4 | 5 | 6 | 7 |
| Polyethylene glycol (n = 12) monolaurate HLB: 14 | 10 | | | 10 | 10 | 10 | 15 |
| Polyethylene glycol (n = 20) monolaurate HLB: 15 | | 10 | | | | | |
| Polyethylene glycol (n = 12) monoisostearate HLB: 12 | | | 10 | | | | |
| Polyethylene glycol (n = 6) caprate HLB: about 8 | | | | | | | |
| Polyethylene glycol (n = 25) octyldodecylate HLB: about 18 | | | | | | | |
| Glycerol | 10 | 10 | 10 | 10 | 10 | 20 | 10 |
| Sodium chloride | | | | 1 | | | |
| Carboxyvinyl polymer | | | | | | | |
| Water | 80 | 80 | 80 | 79 | 80 | 70 | 75 |
| Sheet* | B | B | B | B | D | B | B |
| Detergency | ○ | ○ | ○ | ○ | ○ | ○ | ○ |
| Detergent speed | ○ | ○ | ○ | ○ | ○ | ○ | ○ |
| Handling property | ○ | ○ | ○ | ○ | ○ | ○ | ○ |
| Feeling upon use | ◎ | ◎ | ◎ | ◎ | ◎ | ◎ | ◎ |
| Irritativeness to skin | Weak | Weak | Weak | Weak | Weak | Weak | Weak |
| Stability | ○ | ○ | ○ | ○ | ○ | ○ | ○ |

TABLE 2

| Component (Wt. %) | Invention product | | | | | |
|---|---|---|---|---|---|---|
| | 8 | 9 | 10 | 11 | 12 | 13 |
| Polyethylene glycol (n = 12) monolaurate HLB: 14 | 10 | | | 10 | 10 | 15 |
| Polyethylene glycol (n = 20) monolaurate HLB: 15 | | 10 | | | | |
| Polyethylene glycol (n = 12) monoisostearate HLB: 12 | | | 10 | | | |
| Polyethylene glycol (n = 6) caprate HLB: about 8 | | | | | | |
| Polyethylene glycol (n = 25) octyldodecylate HLB: about 18 | | | | | | |
| Glycerol | 10 | 10 | 10 | 10 | 20 | 10 |
| Sodium chloride | | | | 1 | | |
| Carboxyvinyl polymer | | | | | | |
| Water | 80 | 80 | 80 | 79 | 70 | 75 |
| Sheet* | A | A | A | A | A | A |
| Detergency | ○ | ○ | ○ | ○ | ○ | ○ |
| Detergent speed | ○ | ○ | ○ | ○ | ○ | ○ |
| Handling property | ○ | ○ | ○ | ○ | ○ | ○ |
| Feeling upon use | ◎ | ◎ | ◎ | ◎ | ◎ | ◎ |
| Irritativeness to skin | Weak | Weak | Weak | Weak | Weak | Weak |
| Stability | ○ | ○ | ○ | ○ | ○ | ○ |

TABLE 3

| Component (wt. %) | Comparative product 1 | 2 | 3 | 4 | 5 | 6 | 7 |
|---|---|---|---|---|---|---|---|
| Polyethylene glycol (n = 12) monolaurate HLB: 14 | 10 | 10 | 10 | 10 | | | |
| Polyethylene glycol (n = 20) monolaurate HLB: 15 | | | | | | | |
| Polyethylene glycol (n = 12) monoisostearate HLB: 12 | | | | | | | |
| Polyethylene glycol (n = 6) caprate HLB: about 8 | | | | | 10 | | |
| Polyethylene glycol (n = 25) octyldodecylate HLB: about 18 | | | | | | 10 | |
| Lauric acid triethanolamine salt | | | | | | | 10 |
| Glycerol | 10 | 10 | | 20 | 10 | 10 | 10 |
| Sodium chloride | | | | | | | |
| Carboxyvinyl polymer | | 0.5 | | | | | |
| Water | 80 | 79.5 | 90 | 70 | 80 | 80 | 80 |
| Sheet* | — | — | B | — | B | B | B |
| Detergency | ○ | △ | △ | ○ | ○ | X | △ |
| Detergent speed | ○ | △ | △ | ○ | ○ | X | △ |
| Handling property | X | X | ○ | X | ○ | ○ | ○ |
| Feeling upon use | ○ | X | ○ | ○ | △ | ○ | X |
| Irritativeness to skin | Weak | Weak | Weak | Medium | Weak | Weak | Strong |
| Stability | ○ | ○ | ○ | X | △ | ○ | ○ |

*Sheet A; Cotton nonwoven fabric (Cotton Ace C040S/A01, product of Unichika, Ltd.), basis weight: 40 g/m$^2$, pickup: 3.5 g/g.
Sheet B; Cotton nonwoven fabric (Cotton Ace C060S/A01, product of Unichika, Ltd.), basis weight: 60 g/m$^2$, pickup: 3.5 g/g.
Sheet C; Cotton nonwoven fabric (Cotton Ace C060S/A01, product of Unichika, Ltd.), basis weight: 60 g/m$^2$, pickup: 5 g/g.
Sheet D; Rayon nonwoven fabric (Pilose PXD0060, product of Omikenshi Co., Ltd.), basis weight: 60 g/m$^2$, pickup: 3.5 g/g.

EXAMPLE 2

An aqueous composition having the following formulation was prepared in accordance with a method known per se in the art. The composition was impregnated to a pickup of 3.5 g/g into a 100%-cotton nonwoven fabric (Cotton Ace C060S/A01, product of Unichika, Ltd.) to produce a skin cleansing sheet.

The skin cleansing sheet thus obtained had high detergency to oily smears and detergent speed, did not smear clothes with its drips, could efficiently cleanse the skin irrespective of the place of use, had low irritativeness to the skin, gave users a lesser feeling of remaining after use, scarcely had a slimy feel and was also good in stability.

| (Component) | (wt. %) |
|---|---|
| Polyethylene glycol (n = 12) monolaurate HLB 13.8 | 10.00 |
| Sorbit solution (70%) | 4.00 |
| Ethanol | 5.00 |
| Methylparaben | 0.20 |
| Ethylparaben | 0.05 |
| Propylparaben | 0.05 |
| Perfume base | 0.05 |
| Purified water | Balance |
| | 100.00 |

EXAMPLE 3

Skin cleansing sheets (pickup of aqueous detergent composition: 3.5 g/g of nonwoven fabric) having their corresponding formulations shown in Table 4 were produced. The thus-obtained sheets were evaluated as to detergency, anti-striking through to smears, feeling upon use and retention of aqueous detergent composition. The results are shown in Tables 1 to 3.

Incidentally, another component than cellulose in the nonwoven fabrics of Invention Products 21 and 22 in Table 4 is polypropylene, and these conjugated fibers have a flat modified cross-section. The fibers of the nonwoven fabrics in Table 4 are all distributed as one layer in the direction of thickness.

Evaluation Methods (1) Detergency:

The evaluation was conducted in the same manner as in Example 1.

(2) Anti-striking through to smears:

A certain amount of a lipstick was applied to the inner side of a human lower arm, and the lipstick was wiped off predetermined times with each of the cleansing sheets under a fixed pressure. A color difference ($\Delta E$) between the front and back surfaces of the sheet after the wiping was measured to rank the anti-striking through to smears in accordance with the following standard:

◎ : Not lower than 70%;

○: Not lower than 50%, but lower than 70%;

△: Not lower than 20%, but lower than 50%;

X: Lower than 20%.

(3) Feeling upon use:

The evaluation was conducted in the same manner as in Example 1.

(4) Retention of aqueous detergent composition:

A certain amount (1 g) of a nonwoven fabric was folded, and a certain amount (3.5 g) of an aqueous detergent composition sample was uniformly impregnated into the nonwoven fabric. The nonwoven fabric was then pressed with fingers to observe the exuded state of the sample, thereby ranking the retention of aqueous detergent composition in accordance with the following standard:

◎ : Not exuded at all;

○: Scarcely exuded;

△: Slightly exuded;

X: Exuded.

TABLE 4

|  |  | Invention product | | | | | | | | |
|---|---|---|---|---|---|---|---|---|---|---|
|  |  | 14 | 15 | 16 | 17 | 18 | 19 | 20 | 21 | 22 |
| Nonwoven fabric | Content of cellulose (wt. %) | 100 | 100 | 100 | 100 | 100 | 100 | 80 | 60 | 100 |
|  | Average basis weight (g/m$^2$) | 40 | 60 | 80 | 100 | 60 | 80 | 60 | 60 | 80 |
|  | Average fineness (d: denier) | 1.5 | 1.5 | 1.5 | 1.5 | 2.0 | 2.0 | 1.5 | 1.5 | 1.5 |
|  | Reflectance (%) | 70 | 70 | 75 | 75 | 80 | 90 | 70 | 70 | 80 |
| Aqueous detergent composition | Polyethylene glycol (n = 12) monolaurate HLB: 14 | 10 | 10 | 10 | 10 | 10 | 10 | 10 | 10 | 10 |
|  | Glycerol | 0 | 0 | 0 | 0 | 0 | 0 | 0 | 0 | 10 |
|  | Water | 90 | 90 | 90 | 90 | 90 | 90 | 90 | 90 | 80 |
| Evaluation | Detergency | ○ | ○ | ○ | ○ | ○ | ○ | ○ | ○ | ◎ |
|  | Anti-striking through to smears | ○ | ◎ | ◎ | ◎ | ◎ | ◎ | ◎ | ◎ | ◎ |
|  | Feeling upon use | ◎ | ◎ | ○ | ○ | ◎ | ○ | ○ | ○ | ○ |
|  | Retention of aqueous detergent | ◎ | ◎ | ◎ | ◎ | ◎ | ◎ | ○ | ○ | ◎ |

EXAMPLE 4

Aqueous detergent compositions having their corresponding formulations shown in Tables 5 to 7 were prepared in accordance with a method known per se in the art and evaluated as to appearance, detergency, detergent speed, feeling upon use and irritativeness to the skin. The results are shown in Tables 5 to 7.

Evaluation Methods (1) Appearance:

The aqueous detergent compositions right after the preparation were visually evaluated as to appearance and ranked in accordance with the following standard:

○: Good;

Δ: Fair;

X: Poor (separation).

(2) Detergency:

A certain amount of a lipstick was applied to the inner side of a human lower arm, and the lipstick was removed by massaging the smeared site predetermined times with each of the detergent compositions under a fixed pressure and then rinsing out the detergent composition. A color difference between before and after the removal of the lipstick was measured to determine the detergency in terms of percentage of color difference. The detergency was ranked in accordance with the same standard as in Example 1.

(3) Detergent speed:

The number of times of massaging required to exhibit the detergency of 70% as calculated out by the above measuring method (2) when a certain amount of a lipstick was applied to the inner side of a human lower arm, and the lipstick was removed by massaging the smeared site with each of the detergent compositions under a fixed pressure was determined, and the detergent speed was ranked in accordance with the same standard as in Example 1.

(4) Feeling upon use:

Expert panelists organoleptically evaluated the detergent compositions as to feeling upon use such as a feeling of remaining, slimy feel and refreshed feeling when each of the detergent compositions was applied to the face of the panelist, the face was massaged for 20 seconds, and the detergent composition was then rinsed out with water. The feeling upon use was ranked in accordance with the same standard as in Example 1.

(5) Irritativeness to the skin:

The evaluation was conducted in the same manner as in Example 1.

TABLE 5

| Component (wt. %) | Invention product | | | | | | | | | |
|---|---|---|---|---|---|---|---|---|---|---|
|  | 23 | 24 | 25 | 26 | 27 | 28 | 29 | 30 | 31 | 32 |
| Polyethylene glycol (n = 12) monolaurate HLB: 14 | 10 |  |  | 10 |  |  | 10 |  |  | 5 |
| Polyethylene glycol (n = 20) monolaurate HLB: 15 |  | 10 |  |  | 10 |  |  | 10 |  | 5 |
| Polyethylene glycol (n = 12) monoisostearate HLB: 12 |  |  | 10 |  |  | 10 |  |  | 10 |  |
| Polyethylene glycol (n = 6) caprate HLB: about 8 |  |  |  |  |  |  |  |  |  |  |
| Polyethylene glycol (n = 25) octyldodecylate HLB: about 18 |  |  |  |  |  |  |  |  |  |  |
| Lauric acid triethanolamine salt |  |  |  |  |  |  |  |  |  |  |
| Glycerol | 10 | 10 | 10 |  |  |  | 10 | 10 | 10 |  |
| Sorbitol |  |  |  | 10 | 10 | 10 |  |  |  | 10 |
| Sodium chloride | 1 | 1 | 1 | 1 | 1 | 1 |  |  |  | 1 |
| Potassium chloride |  |  |  |  |  |  | 1 | 1 | 1 |  |
| Carboxyvinyl polymer |  |  |  |  |  |  |  |  |  |  |
| Water | 79 | 79 | 79 | 79 | 79 | 79 | 79 | 79 | 79 | 79 |
| Appearance | ○ | ○ | ○ | ○ | ○ | ○ | ○ | ○ | ○ | ○ |
| Detergency | ◎ | ○ | ○ | ◎ | ○ | ○ | ○ | ○ | ○ | ○ |
| Detergent speed | ○ | ○ | ○ | ○ | ○ | ○ | ○ | ○ | ○ | ○ |

TABLE 5-continued

| | Invention product | | | | | | | | | |
|---|---|---|---|---|---|---|---|---|---|---|
| Component (wt. %) | 23 | 24 | 25 | 26 | 27 | 28 | 29 | 30 | 31 | 32 |
| Feeling upon use | ○ | ○ | ○ | ○ | ○ | ○ | ○ | ○ | ○ | ○ |
| Irritativeness to skin | Weak | Weak | Weak | Weak | Weak | Weak | Weak | Weak | Weak | Weak |

TABLE 6

| | Invention product | | | | | | | |
|---|---|---|---|---|---|---|---|---|
| Component (wt. %) | 33 | 34 | 35 | 36 | 37 | 38 | 39 | 40 |
| Polyethylene glycol (n = 12) monolaurate HLB: 14 | 5 | | | 10 | | | 5 | 10 |
| Polyethylene glycol (n = 20) monolaurate HLB: 15 | | 5 | | | 10 | | 5 | |
| Polyethylene glycol (n = 12) monoisostearate HLB: 12 | | | 5 | | | 10 | | |
| Polyethylene glycol (n = 6) caprate HLB: about 8 | | | | | | | | |
| Polyethylene glycol (n = 25) octyldodecylate HLB: about 18 | | | | | | | | |
| Lauric acid triethanolamine salt | | | | | | | | |
| Glycerol | 15 | 15 | 15 | 5 | 5 | 5 | | |
| Sorbitol | | | | | | | 10 | 5 |
| Sodium chloride | 1 | 1 | 1 | 2 | 2 | 2 | 1 | 2 |
| Potassium chloride | | | | | | | 1 | |
| Carboxyvinyl polymer | | | | | | | | |
| Water | 79 | 79 | 79 | 83 | 83 | 83 | 78 | 83 |
| Appearance | ○ | ○ | ○ | ○ | ○ | ○ | ○ | ○ |
| Detergency | ○ | ○ | ○ | ○ | ○ | ○ | ○ | ○ |
| Detergent speed | ○ | ○ | ○ | ○ | ○ | ○ | ○ | ○ |
| Feeling upon use | ⊚ | ⊚ | ⊚ | ○ | ○ | ○ | ○ | ○ |
| Irritativeness to skin | Weak | Weak | Weak | Weak | Weak | Weak | Weak | Weak |

TABLE 7

| | Comparative product | | | | | | | | | |
|---|---|---|---|---|---|---|---|---|---|---|
| Component (wt. %) | 8 | 9 | 10 | 11 | 12 | 13 | 14 | 15 | 16 | 17 |
| Polyethylene glycol (n = 12) monolaurate HLB: 14 | 10 | 10 | 10 | | | | | | | 10 |
| Polyethylene glycol (n = 20) monolaurate HLB: 15 | | | | | | | | | | |
| Polyethylene glycol (n = 12) monoisostearate HLB: 12 | | | | | | | | | | |
| Polyethylene glycol (n = 6) caprate HLB: about 8 | | | | | | | 10 | | | |
| Polyethylene glycol (n = 25) octyldodecylate HLB: about 18 | | | | | | | | 10 | | |
| Lauric acid triethanolamine salt | | | | | | | 10 | | | |
| Glycerol | | 10 | | 10 | 10 | | 10 | 10 | 10 | 10 |
| Sorbitol | | | | | | | | | | |
| Sodium chloride | | | 1 | 1 | | 1 | 1 | 1 | 1 | 1 |
| Potassium chloride | | | | | | | | | | |
| Carboxyvinyl polymer | | | | | | | | | | 0.4 |
| Water | 90 | 80 | 8 | 8 | 90 | 99 | 79 | 79 | 79 | 79.6 |
| Appearance | ○ | ○ | ○ | ○ | ○ | ○ | ○ | X | ○ | ○ |
| Detergency | Δ | Δ | Δ | X | X | X | Δ | — | X | Δ |
| Detergent speed | X | X | X | X | X | X | Δ | — | Δ | X |
| Feeling upon use | ○ | ○ | ○ | ○ | ○ | ○ | X | — | ○ | X |
| Irritativeness to skin | Weak | Weak | Weak | Weak | Weak | Weak | Strong | — | Weak | Weak |

EXAMPLE 5

An aqueous detergent composition having the following formulation was prepared in accordance with a method known per se in the art.

The detergent composition thus obtained had high detergency to oily smears and detergent speed, and low irritativeness to the skin, gave users a lesser feeling of remaining after use, scarcely had a slimy feel, and could be stably used at a place of high temperature and humidity.

| (Component) | (wt. %) |
|---|---|
| Polyethylene glycol (n = 12) monolaurate HLB 13.8 | 10.00 |
| Sorbit solution (70%) | 4.00 |
| Ethanol | 5.00 |
| Sodium chloride | 2.00 |
| Methylparaben | 0.20 |

| (Component) | (wt. %) |
|---|---|
| Ethylparaben | 0.05 |
| Propylparaben | 0.05 |
| Perfume base | 0.05 |
| Purified water | Balance |
| | 100.00 |

This application is based on Japanese patent applications; No. 090689/1997, filed Apr. 9, 1997, No. 117923/1997, filed May 8, 1997 and No. 146271/1997, filed Jun. 4, 1997, which are herein incorporated by reference.

What is claimed is:

1. A skin cleansing sheet obtained by impregnating (c) a sheet with an aqueous composition containing (a) 1–50 wt. % of a nonionic surfactant having an HLB of 10–16 and (b) 1–30 wt. % of a polyhydric alcohol or glycol ether.

2. The skin cleansing sheet according to claim 1, wherein the component (a) is a nonionic surfactant represented by the following general formula (1):

$$RCOO-(CH_2CH_2O)_n-H \quad (1)$$

wherein RCO is a saturated or unsaturated acyl group having 4–30 carbon atoms, and n is a number of 1–50 on the weight average.

3. The skin cleansing sheet according to claim 1, wherein the component (b) is ethylene glycol, propylene glycol, isoprene glycol, dipropylene glycol, glycerol, 1,3-butylene glycol, sorbitol or diethylene glycol monoethyl ether.

4. The skin cleansing sheet according to any one of claims 1 to 3, wherein the sheet (c) is a woven fabric or nonwoven fabric of natural fibers or synthetic fibers.

5. The skin cleansing sheet according to any one of claims 1 to 3, wherein the sheet (c) is a nonwoven fabric, wherein
   (1) the content of cellulose is at least 50 wt. %;
   (2) the average basis weight is 20–120 g/m²;
   (3) the average fineness of constituent fibers is at most 3 d (deniers);
   (4) it is a nonwoven fabric fabricated by water-jet intermingement; and
   (5) the reflectance is at least 45% when measured in a dry state.

6. The skin cleansing sheet according to claim 1, wherein the aqueous composition further comprises (d) 0.1–10 wt. % of a salt.

7. The skin cleansing sheet according to claim 6, wherein the salt (d) is selected from the group consisting of:
   the sulfates of metals selected from among Groups 1A, 2A, 2B and 3B of the periodic table, the sulfates of non-metallic ions and alkali metal carbonates;
   the sulfates of metals selected from Group 1B of the periodic table, alum, alkali metal hydrogencarbonates, alkali metal tripolyphosphates and pyrophosphates, sodium chloride, potassium chloride, ammonium chloride, and alkali metal silicates; and
   the citrates, tartrates, succinates and carboxymethyloxy succinates of metals selected from the Groups 1A, 2A, 2B and 3B of the periodic table, the citrate, tartrate, succinate and carboxymethoyloxy succinates of an ammonium ion.

8. An aqueous skin detergent composition comprising the following components (a), (b) and (d):
   (a) 1–50 of a nonionic surfactant having an HLB of 10–16;
   (b) 1–30 wt. % of a polyhydric alcohol or glycol ether; and
   (d) 0.1–10 wt. % of a salt.

9. The skin cleaning sheet according to claim 1, consisting essentially of an aqueous composition of defined components (a) and (b).

10. The aqueous skin detergent composition according to claim 8, consisting essentially of defined components (a), (b) and (d).

* * * * *